United States Patent
Kobayashi

(10) Patent No.: US 7,375,244 B2
(45) Date of Patent: May 20, 2008

(54) PRODUCTION METHOD FOR AMINOPHOSPHONIC ACID DERIVATIVES

(75) Inventor: Shu Kobayashi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 85 days.

(21) Appl. No.: 10/591,964

(22) PCT Filed: Mar. 7, 2005

(86) PCT No.: PCT/JP2005/003851

§ 371 (c)(1),
(2), (4) Date: Sep. 6, 2006

(87) PCT Pub. No.: WO2005/085262

PCT Pub. Date: Sep. 15, 2005

(65) Prior Publication Data

US 2007/0142658 A1    Jun. 21, 2007

(30) Foreign Application Priority Data

Mar. 9, 2004    (JP) .............................. 2004-065251

(51) Int. Cl.
*C07F 9/02*    (2006.01)

(52) U.S. Cl. ...................................... 558/145

(58) Field of Classification Search ..................... None
See application file for complete search history.

(56) References Cited

FOREIGN PATENT DOCUMENTS

JP    2003-260363    9/2003

OTHER PUBLICATIONS

Chollet-Gravey, et al., "A preparative synthesis of 1-amino-3-hydroxypropylphosphonic acid", Synthetic Commun. 21, 1847-1858 (1991).
Merrett et al., "The synthesis and Rotational Isomerism of 1-amino-1-imadizol-4-ylethylphosphonic acid", J. Chem. Soc. Perkin Trans 1 (1988) pp. 61-67.
Schrader et al., "Synthese von 1-aminophosphonsaure-derivaten uber Acyliminophosphonsaure-ester", Synthesis 1986, pp. 372-375.
Vasella et al., "Asymmetric Synthesis of a-amionphosphonic acids by cycloaddition . . . ", Helv. Chim. Acta 65 (1982) pp. 1953-1964.
Kobayashi et al., "Catalytic, assymetric mannich-type reactions of N-acylimino esters . . . ", JACS 2003, vol. 125, pp. 2507-2515.

*Primary Examiner*—Paul A. Zucker
(74) *Attorney, Agent, or Firm*—Gary C Cohn PLLC

(57) ABSTRACT

To present a reaction system that efficiently catalyzes an enantio selective asymmetric nucleophilic addition reaction of an α-iminophosphonic acid ester. An optically active α-amino-γ-oxophosphonic acid derivative is produced through an asymmetric addition reaction of an α-iminophosphonic acid ester and a nucleophilic agent (for example, a silyl enol ether).

10 Claims, No Drawings

PRODUCTION METHOD FOR AMINOPHOSPHONIC ACID DERIVATIVES

FIELD OF THE INVENTION

This invention relates to a production method for aminophosphonic acid derivatives through a reaction of an α-iminophosphonate ester and a nucleophilic agent in the presence of a chiral copper catalyst and, more particularly, to a production method for optically active aminophosphonic acid derivatives through an asymmetric addition reaction of an α-iminophosphonate ester and a nucleophilic agent in the presence of a chiral copper catalyst.

PRIOR ART

Although αaminophosphonic acid derivatives occupy an important position as analogues of α-amino acids in pharmacological and biochemical fields (Reference 1), a synthetic method for producing optically active α-aminophosphonic acid derivatives have not yet been established. The conventional production method for α-aminophosphonic acid derivatives has excellent stereo selectivity, but an asymmetric source yielding a stoichiometric amount of optically active α-aminophosphonic acid derivatives was not yet known (References 2 and 3). Shibasaki et al recently reported a hydrophosphonylation of imines using a catalytic amount of an asymmetric metal catalyst (References 4 and 5), but a more efficient method with a better general application is needed.

The inventors have been investigating reactions involving asymmetric catalysts utilizing various metals, ligands and reaction substrates and recently discovered an efficient method to produce α-aminoacid derivatives from N-acyl iminoesters using a chiral copper catalyst (Reference 6 and 7).

Reference 1: Kafarski, P.; Lejczak, B. Aminophosphonic and Aminophosphinic Acids; Kukhar, V. P.; Hudson, H. R. Ed.; John Wiley and Sons, 2000; Chap. 12, p 407.

Reference 2: Schöllkopf, U.; Schütze, R. Liebigs Ann. Chem. 1987, 45.

Reference 3: Schrader, T.; Kober, R.; Steglich, W. Synthesis 1986, 372.

Reference 4: Sasai, H.; Arai, S.; Tahara, Y.; Shibasaki, M. J. Org. Chem. 1995, 60, 6656.

Reference 5: Kukhar, V. P. Aminophosphonic and Aminophosphinic Acids; Kukhar, V. P.; Hudson, H. R. Ed.; John Wiley and Sons, 2000; Chap. 5, p 127.

Reference 6: Kobayashi, S.; Matsubara, R.; Nakamura, Y.; Kitagawa, H.; Sugiura, M. J. Am. Chem. Soc. 2003, 125, 2507.

Reference 7: Japanese Patent Application Public Disclosure (Kokai) No. 2003-260363

PROBLEMS TO BE SOLVED BY THE INVENTION

The objective of the present invention is to provide a reaction system that efficiently catalyzes an enantio selective asymmetric nucleophilic addition reaction of an α-iminophosphonic acid ester.

However, an α-aminophosphonic acid ester is a stronger Lewis base than an N-acylimino ester, and the dissociation of copper atoms of the active centers of the Lewis acid catalyst from a reaction product becomes slow in the same reaction system and it was anticipated that the reaction rate and enantio selectivity will decine.

MEANS TO SOLVE THE PROBLEM

That is, the present invention is a production method for aminophosphonic acid derivatives comprising reacting an α-iminophosphonate ester represented by the formula below

[Chemical Formula 1]

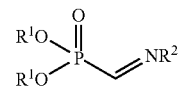

wherein $R^1$ represents an alkyl group and $R^2$ represents a protective group for an amino group, and a nucleophilic agent in the presence of a chiral copper catalyst represented by the formula below

[Chemical Formula 2]

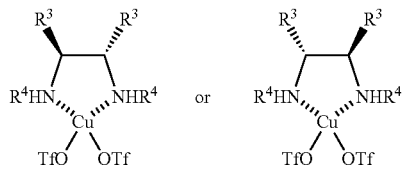

wherein $R^3$ and $R^4$, may be identical or different, represent an aryl group or an aralkyl group.

Advantage of the Invention

A silyl enolate addition reaction on an α-iminophosphonic acid ester using a chiral copper catalyst of the present invention proceeds with excellent chemical and asymmetric yield when a suitable additive, particularly HFIP and the like, is added, and corresponding N-protected-α-amino-γ-oxophosphonic acid derivatives can be obtained.

DETAILED DESCRIPTION OF THE INVENTION

The chiral copper catalyst used in the reaction system is represented by the following formula.

[Chemical Formula 2]

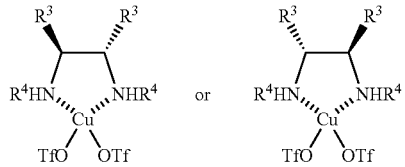

In the formula, $R^3$ and $R^4$ may be identical or different and represent aryl groups or aralkyl groups. Phenyl and naphthyl groups are preferred as the aryl group, and these aromatic rings may also contain substituents. The same applies to the aromatic rings in the aralkyl group. OTf represents $OSO_2CF_3$ (triflate).

This catalyst exhibits excellent enantio selectivity in an asymmetric addition reaction of an imine and is prepared from copper (II) triflate and a chiral diamine represented by the following formula.

[Chemical Formula 5]

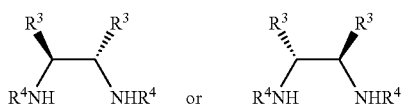

In the formula, $R^3$ and $R^4$ are as defined previously.

α-Iminophosphonic acid ester, the reaction material of the present invention, is represented by the following formula.

[Chemical Formula 1]

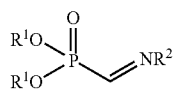

$R^1$s may be identical or different, but they are preferably identical and are alkyl groups, preferably alkyl groups having 1 to 4 carbon atoms.

$R^2$ represents a protective group for an amino group. This amino protective group includes Troc (trichloroethoxy carbonyl, $Cl_3CCH_2OCO-$), Boc (t-butoxycarbonyl), Teoc (trimethyl silyl ethoxycarbonyl, $Me_3SiCH_2CH_2OCO-$), Ac (acetyl group), an acyl group such as $CH_3(CH_2)_nCO-$ and the like. However, a urethane type amino protective group is preferred, and Troc (group) is particularly preferred.

The α-iminophosphonic acid diester used as a synthesis raw material may be obtained as an imine from N-protected-α-aminobromomethyl phosphonic acid diester using a polymer immobilized piperidine, and the solution obtained by removing the polymer component using filtration may be used without any further treatment.

As a nuclephilic agent, an allyl silane compound such as ally trichlorosilane and the like may be cited, but the silyl enol ether represented by the following formula is preferred.

[Chemical Formula 3]

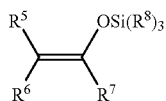

$R^5$ and $R^6$ may be identical or different and represent hydrogen atoms, alkyl groups, aryl groups or aralkyl groups. They together preferably represent hydrogen atoms.

$R^7$ represents an alkyl group, aryl group, aralkyl group, alkoxy group or sulfide group. This sulfide group is represented by $-SR^9$; wherein $R^9$ represents an alkyl group or an aryl group and preferably represents an alkyl group having 1 to 10 carbon atoms or a phenyl group that may also contain substituents.

For $R^5$ to $R^7$, phenyl groups and naphthyl groups may be cited as aryl groups and benzyl groups may be cited as aralkyl groups. These aromatic rings may also contain substituents such as halogen atoms, short chain alkyl groups, hydroxyl groups, amino groups, nitro groups and the like.

$R^8$s may be identical or different and represent alkyl groups or phenyl groups. $Si(R^8)_3$ is preferably $SiMe_3$, $SiEt_3$, $Si(i-C_7H_3)_3$, $Si(Ph)_2(t-C_4H_9)$ or $Si(Me)_2(t-C_4H_9)$.

A compound having an activated proton such as, for example, water, alcohols and carboxylic acids may be optionally added to this reaction medium.

The effect of this additive in an addition reaction of a silyl enol ether with an α-iminophosphonic acid ester was studied by using a chiral copper catalyst (Chemical formula 2). At this point, a trimethyl silyl enol ether derived from benzaldehyde was used as the silyl enol ether and N-(2,2,2-trichloroethoxy carbonyl) iminomethyl phosphonic acid diethyl ester was used as the α-iminophosphonic acid ester.

Various additives were studied. As a result, hexafluoro isopropyl alcohol (HFIP) (Tetrahedron 1997, 53, 17015; J. Am. Chem. Soc., 2001, 123, 4480) was found to be effective as an additive to this reaction medium.

TABLE 1

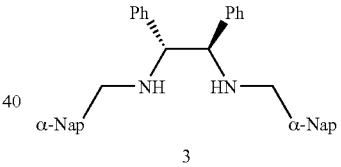

| Entry | additive | yield (%) | ee (%) |
|---|---|---|---|
| 1 | none | 78 | 49 |
| 2 | HFIP (1.0 eq) | 87 | 65 |
| 3[a] | HFIP (1.0 eq) | 81 | 89 |
| 4[ab] | HFIP (1.0 eq) | 78 | 93 |
| 5[ab] | HFIP (2.0 eq) | 82 | 92 |
| 6[ab] | HFIP (2.0 eq), MS3A (50 g/mol) | 86 | 91 |

[a] 1 was slowly added for 8.0 h.
[b] 2a was slowly added for 8.0 h.

As a result of this study, the addition of HFIP and molecular sieve 3A was found clearly effective on both chemical and asymmetric yields in this reaction system. Almost the same chemical and asymmetric yields could be achieved even when no HFIP was added by conducting the addition of the catalyst to the substrate over 48 hours.

An optically active α-aminophosphonic acid derivative represented by the formula below is obtained when the α-iminophosphonic acid ester described above and a silyl enol ether are allowed to react using an asymmetric catalyst reaction system of the present invention.

[Chemical formula 4]

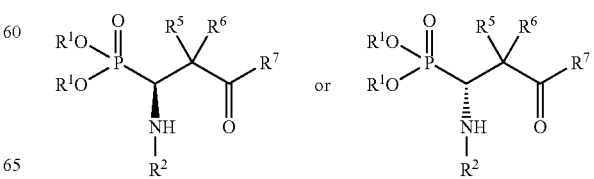

In the formula, $R^1$, $R^2$, $R^4$, $R^5$ and $R^7$ are as defined previously.

This asymmetric catalyst reaction system is preferably prepared as described below.

Copper (II) triflate and a chiral diamine are mixed in an organic solvent and appropriately agitated. The organic solvent used here may be a hydrocarbon or a halogenated hydrocarbon. Of these, methylene chloride, toluene or their mixtures are ideal, and an amount of solvent providing a range of from 0.01 M to 0.2 M in terms of the reaction substrate concentration is ideal. The preparation temperature for the catalyst system is not particularly restricted, but about room temperature is convenient when mixing. The aging time for the catalyst is considered appropriately, and from 30 minutes to 24 hours is ordinarily used with the range of from 3 hours to 6 hours preferred. The copper (II) triflate to chiral diamine ratio is from 1:1 to 1:2, and from 1:1.0 to 1:1.2 is preferred. The amount of the catalyst used is from 0.1% to 30% per the reaction substrate, and from 5% to 20% is preferred.

Next a molecular sieve is added, and HFIP is subsequently added. The amount of molecular sieve is in the range that does not interfere the agitation, and from 10 mg to 500 mg per 1 mmole of substrate is used with from 50 mg to 300 mg preferred. A silyl enol ether is preferably added at about 0° C. HFIP is added upon appropriately diluting it with a solvent, and the amount used is appropriately decided between 0 to 5 equivalents per the substrate but from 0 to 2 equivalents is preferred.

Lastly, a silyl enol ether compound solution is added to a catalyst system prepared in the manner described above, and an α-iminophosphonic acid diester solution is subsequently added. The addition rate exerts an extensive influence on the reaction. The addition is ordinarily conducted over about 2 to 20 hours. However, better results are frequently and generally realized when the addition is conducted slowly, and the addition time is sometimes extended as necessary.

The α-amino-γ-oxophosphonic acid derivatives obtained using the catalyst reaction system can be converted readily into aspartic acid analogues (Chemical formula 6) and compounds useful as enzyme interfering agents (Chemical formula 7) using the route described below. In addition, the γ-position carbonyl group can also be converted into a methylene group (Chemical formula 8).

[Chemical formula 6]

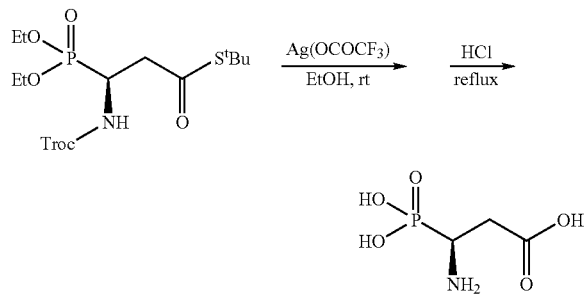

[Chemical formula 7]

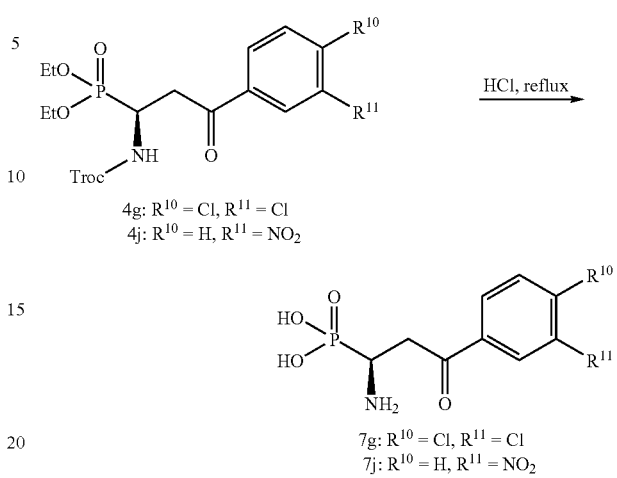

[Chemical formula 8]

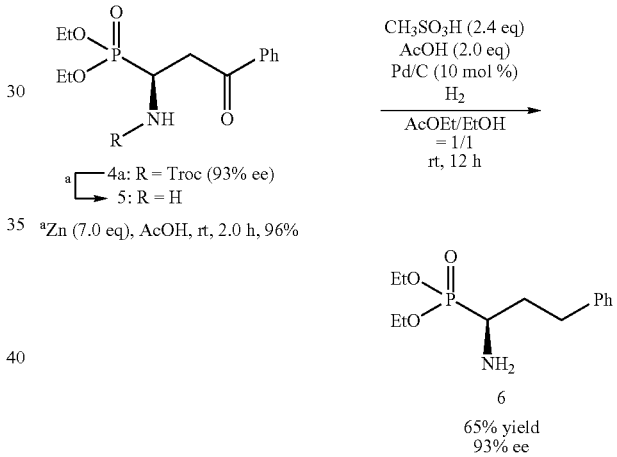

The present invention is illustrated using the Examples below, but the Examples are not presented with the intention of restricting the present invention.

In the Examples below, various properties were measured using the devices and methods shown below.

(1) NMR spectrum: JEOL-LA300, JEOL-LA400 or LEOL-LA500 (manufactured by Nihon Electronic K.K.) was used.

(2) IR spectrum: JASCO FT/IR-610 (manufactured by Nihon Bunko K.K.) was used.

(3) Angle of rotation: JASCO P-1010 (manufactured by Nihon Bunko K.K.) was used.

A silyl enol ether was synthesized according to the reference below (1), and the starting material for synthesis of an iminophosphonic acid ester was synthesized according to the method described in the reference (2) below. Other reagents were all purchased as commercially available products, and they were used upon purification as needed. The reactions were all conducted under argon atmosphere.

(1) a) Colvin, E. W. Silicon Reagents in Organic Synthesis; Academic: New York, 1988; Chapter 15.1. b) Gennari, C; Beretta, M. G.; Bernarde, A.; Moro, G.; Scolastico, C.; Todeschini, R. Tetrahedron 1986, 42, 893. c) Walshe, N. D. A.; Goodwin, G. B. T.; Smith, G. C.; Woodward, F. E. Org. Synth. 1987, 65. 1.

(2) a) Schrader, T.; Kober, R.; Steglich, W. Synthesis 1986, 372. b) Kobayashi, S.; Matsubara, R.; Nakamura, Y.; Kitagawa, H.; Sugiura, M. J. Am. Chem. Soc. 2003, 125, 2507.

PRODUCTION EXAMPLE 1

Preparation of an Iminophosphonic Acid Diester Solution

Piperidinomethyl polystyrene (3.7 mmoles/g, 2,243 mg, 0.9 mmole) and molecular sieve 4A (30 mg) were added to a methylene chloride (3.0 ml) solution of diethyl bromo-(2,2,2-trichloroethoxycarbonyl amino) methylphosphonate (0.3 mmole). The reaction solution was agitated for 20 minutes at room temperature, filtered using a membrane filter (Whatman 0.15 μm) and the filtrate was used in a reaction without any further treatment.

EXAMPLE 1

Silyl Enol Ether Addition Reaction on an Iminophosphonic Acid Diester Using a Chiral Copper Catalyst in the Co-presence of HFIP Methylene chloride (1.5 ml) was added to copper triflate (20 μmoles) and a chiral diamine (22 μmoles), and the reaction mixture was agitated for 6 hours at room temperature. Molecular sieve 3A (10 mg) was added, and the reaction mixture was subsequently cooled to 0° C. A methylene chloride (0.5 ml) solution of the nucleophilic agent (a silyl enol ether, 0.1 mmole) shown in Table 2 and a methylene chloride (0.5 ml) solution of HFIP (0.4 mmole) were added. A methylene chloride (0.1 M, 2 ml) solution of the N-protected-α-iminophosphonic acid diester obtained in Production Example 1 and a methylene chloride (2 ml) solution of a silyl enol ether (0.2 mmole) again were slowly (ordinarily over eight hours) added dropwise. The reaction mixture was agitated for an additional hour. The reaction solution was poured into a saturated aqueous solution of sodium bicarbonate and was agitated vigorously until the organic layer changed to blue. The organic layer was extracted using methylene chloride. The organic layers were combined, washed using saturated aqueous sodium chloride solution and dried using anhydrous sodium sulfate. The solvent was removed by distillation under reduced pressure, and the residue was purified using silica gel chromatography to obtain a desired N-protected-α-amino-γ-oxophosphonic acid diester derivative.

Nucleophilic agents, products, reaction yields and optical purity are shown in Table 2.

TABLE 2

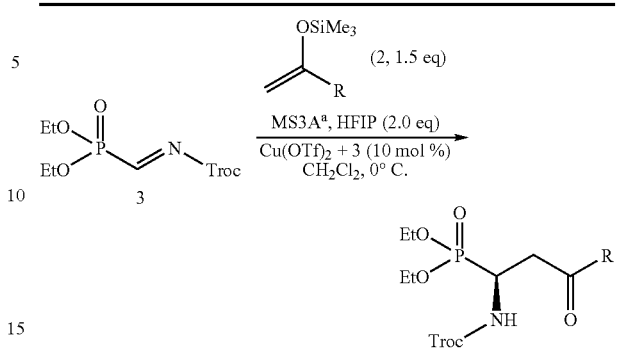

| Entry[b] | Nucleophile | Product | Yield (%) | ee (%) |
|---|---|---|---|---|
| 1 | 2a | 4a | 86 | 91 |
| 2 | 2b | 4b | 82 | 85 |
| 3 | 2c | 4c | 71 | 91 |
| 4 | 2d | 4d | 86 | 86 |
| 5 | 2e | 4e | 80 | 89 |
| 6 | 2f | 4f | 82 | 76 |
| 7 | 2g | 4g | 83 | 92 |
| 8 | 2h | 4h | 79 | 92 |
| 9 | 2i | 4i | 84 | 87 |
| 10 | 2j | 4j | 88 | 94 |
| 11 | 2k | 4k | 70 | 89 |
| 12 | 2l | 4l | 69 | 90 |

[a] 50 g/mol
[b] 1 and 2 were slowly added for 8 h.

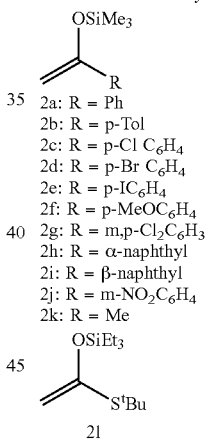

2a: R = Ph
2b: R = p-Tol
2c: R = p-Cl $C_6H_4$
2d: R = p-Br $C_6H_4$
2e: R = p-I$C_6H_4$
2f: R = p-MeO$C_6H_4$
2g: R = m,p-$Cl_2C_6H_3$
2h: R = α-naphthyl
2i: R = β-naphthyl
2j: R = m-$NO_2C_6H_4$
2k: R = Me OSiEt$_3$ S$^t$Bu

21

The properties of the N-trichloroethoxycarbonyl-α-amino-γ-oxophosphonic acid diethyl ester obtained according to the synthesis described above are shown below.

(1S-[Oxo-3-phenyl-1-(2,2,2-trichloro-ethoxycarbonylamino)-propyl]-phosphonic acid diethyl ester (4a): $[\alpha]^{27}_D$ –6.34 (92% ee, c 0.99, CHCl$_3$); $^1$H NMR (CDCl$_3$) δ=7.96 (2H, m), 7.59 (1H, m), 7.47 (2H, m), 4.81 (1H, d, J=12.0 Hz), 4.66 (1H, d, J=12.2 Hz), 4.9-4.7 (1H, m), 4.2-4.1 (4H, m), 3.6-3.35 (2H, m), 1.32 (3H, t, J=7.0 Hz), 1.29 (3H, t, J=7.4 Hz); $^{13}$C NMR (CDCl$_3$) δ=196.0 (d, J=10.7 Hz), 154.0 (d, J=5.7 Hz), 136.2 (s), 133.5 (s), 128.7 (s), 128.1 (s), 95.3 (s), 74.7 (s), 63.2 (J=6.5 Hz), 62.8 (J=6.3 Hz), 44.4 (d, J=160.0 Hz), 38.2 (d, J=4.2 Hz), 16.3 (J=5.8 Hz), 16.3 (J=5.8 Hz); IR 3743, 3239, 3053, 2982, 2360, 1739, 1691, 1598, 1579, 1544, 1449, 1393, 1367, 1229, 1146, 1031, 972, 819, 757, 737 cm$^{-1}$; Chiral HPLC, Daicel Chiralcel AD, hexane/iPrOH=9/1, flow rate=1.0 mL/min; $t_R$=18.4 min (R), $t_R$=23.0 min (S)

(1S)-[3-Oxo-3-p-tolyl-1-(2,2,2-trichloro-ethoxycarbonylamino)-propyl]-phosphonic acid diethyl ester (4b): [α]$^{26}$$_D$ −4.50 (85% ee, c 1.63, CHCl$_3$); $^1$H NMR (CDCl$_3$) δ=7.86 (2H m), 7.27 (2H, m), 4.81 (1H, d, J=12.0 Hz), 4.66 (1H, d, J=12.2 Hz), 4.9-4.7 (1H, m), 3.6-3.35 (2H, m), 1.32 (3H, t, J=7.0 Hz), 1.29 (3H, t, J=7.4 Hz); $^{13}$C NMR (CDCl$_3$) δ=195.7 (d, J=9.8 Hz), 154.1 (s), 144.5 (s), 133.8 (s), 129.4 (s), 128.3 (s), 95.4 (s), 74.7 (s), 63.2 (d, J=6.6 Hz), 62.8 (d, J=6.5 Hz), 44.7 (d, J=160.4 Hz), 38.1 (s), 16.5 (d, J=5.8 Hz), 16.3 (d, J=5.8 Hz); IR 3432, 3241, 3047, 2981, 2099, 1739, 1686, 1607, 1545, 1439, 1410, 1367, 1231, 1183, 1147, 1031, 978, 817, 766, 736, 542, 465 cm$^{−1}$; Chiral HPLC, Daicel Chiralcel AD, hexane/iPrOH=9/1, flow rate=1.0 mL/min; $t_R$=19.4 min (minor, R), $t_R$=25.9 min (major, S) Anal. Calcd for C$_{17}$H$_{23}$Cl$_3$NO$_6$P C:43.01, H:4.88, N: 2.95. Found C:42.75, H:5.12, N:2.98

(1S)-[3-(4-Chloro-phenyl)-3-oxo-1-(2,2,2-trichloro-ethoxycarbonylamino)-propyl]-phosphonic acid diethyl ester (4c): [α]$^{26}$$_D$−2.71 (91% ee, c 0.56, CHCl$_3$); $^1$H NMR (CDCl$_3$) δ=7.90 (2H, m), 7.46 (2H, m), 5.74 (1H, d, J=9.8 Hz), 4.80 (1H, d, J=12.0 Hz), 4.67 (1H, d, J=12.0 Hz), 4.9-4.7 (1H, m), 4.2-4.1 (4H, m), 3.6-3.35 (2H, m), 1.32 (3H, t, J=7.0 Hz), 1.29 (3H, t, J=7.4 Hz); $^{13}$C NMR (CDCl$_3$) δ=194.9 (s), 154.0 (s), 135.0 (s), 132.1 (s), 129.7 (s), 128.9 (s), 95.3 (s), 74.8 (s), 63.3 (d, J=7.5 Hz), 62.9 (d, J=7.4 Hz), 44.5 (d, J=160.5 Hz), 38.3 (s), 16.5 (d, J=5.8 Hz), 16.3 (d, J=5.8 Hz); IR 3437, 3060, 2988, 2360, 2092, 1742, 1685, 1627, 1544, 1470, 1392, 1369, 1260, 1220, 1146, 1124, 1081, 1030, 968, 861 cm$^{−1}$; Chiral HPLC, Daicel Chiralcel AD, hexane/iPrOH=9/1, flow rate=1.0 mL/min; tR=21.8 min (R), tR=34.5 min (S) Anal. Calcd for C$_{16}$H$_{21}$Cl$_3$NO$_6$P C: 38.81 H: 4.07 N: 2.83. Found C: 39.01 H: 4.37 N: 2.83

(1S)-[3-(4-Bromo-phenyl)-3-oxo-1-(2,2,2-trichloro-ethoxycarbonylamino)-propyl]-phosphonic acid diethyl ester (4d): [α]$^{26}$$_D$−5.63 (92% ee, c 4.33, CHCl$_3$); $^1$H NMR (CDCl$_3$) δ=7.82 (2H, m), 7.62 (2H, m), 6.03-5.90 (1H, m), 4.80 (1H, d, J=12.0 Hz), 4.66 (1H, d), 4.90-4.60 (1H, m), 4.20-4.11 (4H, m), 3.51-3.35 (2H, m), 1.32 (3H, t, J=7.1 Hz), 1.30 (3H, t, J=7.1 Hz); $^{13}$C NMR (CDCl$_3$) δ=195.1, 154.0, 135.0, 132.1, 129.7, 128.9, 95.3, 74.8, 63.3 (d, J=7.5 Hz), 62.9 (d, J=7.4 Hz), 44.5 (d, J=160.5 Hz), 38.3, 16.5 (d, J=5.8 Hz), 16.3 (d, J=5.8 Hz); IR 3447, 2989, 2084, 1735, 1683, 1641, 1586, 1545, 1395, 1227, 1151, 1029, 976, 813, 728, 548 cm$^{−1}$; LRMS (FAB) m/z=[M+H]$^+$; HRMS (FAB); Exact mass calcd for C$_{16}$H$_{12}$BrCl$_3$NO$_6$P [M+H]+, 537.9355. Found 537.9343; HPLC, Daicel Chiralcel AD, hexane/iPrOH=9/1, flow rate=1.0 mL/min, $t_R$=21.5 min (R), $t_R$=34.5 min (S).

(1S)-[3-(4-Iodo-phenyl)-3-oxo-1-(2,2,2-trichloro-ethoxycarbonylamino)-propyl]-phosphonic acid diethyl ester (4e): [α]$^{27}$$_D$−5.67 (89% ee, c 1.89, CHCl$_3$); $^1$H NMR (CDCl$_3$) δ=7.84 (2H, m), 7.66 (2H, m), 6.3-5.8 (1H, m), 4.80 (1H, d, J=12.1 Hz), 4.66 (1H, d, J=11.9 Hz), 4.9-4.6 (1H, m), 4.2-4.1 (4H, m), 3.55-3.30 (2H, m), 1.35-1.25 (6H, m); $^{13}$C NMR (CDCl$_3$) δ=195.4, 154.0, 138.1, 135.5, 129.5, 101.8, 95.3, 74.7, 63.4 (d, J=6.8 Hz), 62.9 (d, J=6.8 Hz), 44.5 (d, J=159.8 Hz), 38.3, 16.5, 16.4 16.3; IR 3436, 3247, 3055, 2981, 2318, 2098, 1738, 1635, 1581, 1541, 1438, 1394, 1367, 1229, 1146, 1082, 979, 819, 730, 549 cm$^{−1}$, Chiral HPLC, Daicel Chiralcel AD, hexane/iPrOH=9/1, flow rate=1.0 mL/min; $t_R$=15.7 min (R), $t_R$=29.7 min (S); Anal. Calcd for C$_{16}$H$_{21}$Cl$_3$NO$_6$P C: 32.76 H: 3.44 N: 2.39. Found C: 32.60 H: 3.58 N: 2.49

(1S)-[3-(4-Methoxy-phenyl)-3-oxo-1-(2,2,2-trichloro-ethoxycarbonylamino)-propyl]-phosphonic acid diethyl ester (4f): [α]$^{26}$$_D$−6.47 (68% ee, c 2.09, CHCl$_3$); $^1$H NMR (CDCl$_3$) δ=7.94 (2H, m), 6.94 (2H, m), 6.1-5.8 (1H, m), 4.81 (1H, d, J=12.2 Hz), 4.65 (1H, d, J=12.2 Hz), 4.8-4.7 (1H, m), 4.2-4.1 (4H, m), 3.55-3.32 (2H, m), 1.32 (3H, t, J=7.1 Hz), 1.29 (3H, t, J=7.1 Hz); $^{13}$C NMR (CDCl$_3$) δ=194.6, 163.9, 154.0, 135.6, 129.4, 129.7, 113.9, 95.4, 74.7, 63.2 (d, J=6.6 Hz), 62.8 (d, J=6.6 Hz), 55.5, 44.7 (d, J=159.7 Hz), 37.8, 16.5 (d, J=4.9 Hz), 16.3 (d, J=5.7 Hz); IR 3473, 2319, 2087, 1680, 1547, 1449, 1398, 1362, 1227, 1150, 1029, 967, 810, 729, 689, 547 cm$^{−1}$; HRMS (FAB); Exact mass calcd for C$_{17}$H$_{24}$Cl$_3$NO$_7$P [M+H]+, 490.0356. Found 490.0374; Chiral HPLC, Daicel Chiralcel AD, hexane/iPrOH=9/1, flow rate=1.0 mL/min; $t_R$=31.0 min (minor, R), $t_R$=47.0 min (major, S)

(1S)-[3-(3,4-Dichloro-phenyl)-3-oxo-1-(2,2,2-trichloro-ethoxycarbonylamino)-propyl]-phosphonic acid diethyl ester (4g): [α]$^{27}$$_D$−5.88 (89% ee, c 4.05, CHCl$_3$); $^1$H NMR (CDCl$_3$) 1H NMR (CDCl$_3$) δ=7.90 (2H, m), 7.46 (2H, m), 5.74 (1H, d, J=9.8 Hz), 4.80 (1H, d, J=12.0 Hz), 4.67 (1H, d, J=12.0 Hz), 4.9-4.7 (1H, m), 4.2-4.1 (4H, m), 3.6-3.35 (2H, m), 1.32 (3H, t, J=7.0 Hz), 1.29 (3H, t, J=7.4 Hz); $^{13}$C NMR (CDCl$_3$) δ=195.1, 154.0, 135.0, 132.1, 129.7, 128.9, 95.3, 74.8, 63.3 (d, J=7.5 Hz), 62.9 (d, J=7.4 Hz), 44.5 (d, J=160.5 Hz), 38.3, 16.5 (d, J=5.8 Hz), 16.3 (d, J=5.8 Hz); IR 3235, 3050, 2981, 2355, 1739, 1687, 1590, 1570, 1540, 1444, 1400, 1367, 1228, 1146, 1094, 1032, 975, 823, 738, 557, 526, 461 cm$^{−1}$; HRMS (FAB); Exact mass calcd for C$_{16}$H$_{20}$Cl$_5$NO$_6$P [M+H]$^+$, 527.9471. Found 527.9496; Chiral HPLC, Daicel Chiralcel AD, hexane/iPrOH=9/1, flow rate=1.0 mL/min; $t_R$=14.4 min (R), $t_R$=26.6 min (S)

(1S)-[3-Naphthalen-1-yl-3-oxo-1-(2,2,2-trichloro-ethoxycarbonylamino)-propyl]-phosphonic acid diethyl ester (4h): [α]$^{27}$$_D$−6.33 (92% ee, c 0.99, CHCl$_3$); $^1$H NMR (CDCl$_3$) δ=8.65 (1H, m), 8.02-7.85 (3H, m), 7.64-7.46 (3H, m), 6.20-5.75 (1H, m), 4.77 (1H, d, J=12.1 Hz), 4.67 (1H, d, J=12.1 Hz), 4.85-4.70 (1H, m), 4.25-4.10 (4H, m), 3.64-3.52 (2H, m), 1.33 (3H, t, J=7.1 Hz), 1.29 (3H, t, J=7.1 Hz); $^{13}$C NMR (CDCl$_3$) δ=199.7, 154.0, 134.7, 134.0, 133.4, 130.1, 128.4, 128.3, 128.2, 126.6, 125.8, 124.3, 95.4, 74.7, 63.3 (d, J=7.4 Hz), 62.9 (d, J=6.8 Hz), 44.9 (d, J=158.9 Hz), 38.3 (s), 16.5, 16.4, 16.3; IR 3430, 3240, 3052, 2987, 2364, 2099, 1744, 1691, 1541, 1508, 1438, 1394, 1370, 1254, 1146, 1099, 1029, 968, 802, 777, 738, 541 cm$^{−1}$; HRMS (FAB); Exact mass calcd for C$_{20}$H$_{23}$Cl$_5$NO$_6$P [M+H]$^+$, 510.0407. Found 510.0422; Chiral HPLC, Daicel Chiralcel AD, hexane/iPrOH=9/1, flow rate=1.0 mL/min; $t_R$=14.3 min (R), $t_R$=21.6 min (S)

(1S)-[3-Naphthalen-2-yl-3-oxo-1-(2,2,2-trichloro-ethoxycarbonylamino)-propyl]-phosphonic acid diethyl ester (4i): [α]$^{25}$$_D$−16.4 (87% ee, c 1.41, CHCl$_3$); $^1$H NMR (CDCl$_3$) δ=8.49 (1H, m), 8.02-7.84 (2H, m), 7.65-7.50 (2H, m), 6.2-6.0 (1H, m), 4.82 (1H, d, J=12.1 Hz), 4.67 (1H, d, J=11.9 Hz), 5.0-4.8 (1H, m), 4.25-4.10 (4H, m), 3.75-3.50 (2H, m), 1.37 (3H, t, J=7.1 Hz), 1.29 (3H, t, J=7.1 Hz); $^{13}$C NMR (CDCl$_3$) δ=196.0, 154.1, 135.7, 133.6, 132.4, 130.2, 129.6, 128.8, 128.6, 127.8, 126.9, 123.7, 95.4 (s), 74.7 (s), 63.3 (d, J=7.4 Hz), 62.9 (d, J=6.8 Hz), 44.7 (d, J=160.4 Hz), 38.3, 16.5 ,16.4, 16.3; IR 3852, 3237, 3056, 2986, 2359, 2102, 1737, 1685, 1628, 1596, 1542, 1469, 1438, 1392, 1369, 1226, 1146, 1124, 1030, 969, 859, 821, 735, 546,476 cm$^{−1}$; Chiral HPLC, Daicel Chiralcel AD, hexane/iPrOH=9/1, flow rate=1.0 mL/min; $t_R$=20.0 min (R), $t_R$=32.1 min (S); Anal. Calcd for C$_{20}$H$_{23}$Cl$_3$NO$_6$P C: 47.03, H:4.54, N:2.74 Found C:47.33, H:4.74, N:2.73

(1S)-[3-(3-Nitro-phenyl)-3-oxo-1-(2,2,2-trichloro-ethoxycarbonylamino)-propyl]-phosphonic acid diethyl ester (4j): [α]$^{27}$$_D$−8.46 (94% ee, c 2.12, CHCl3); $^1$H NMR (CDCl$_3$) δ=7.90 (2H, m), 7.46 (2H, m), 5.74 (1H, d, J=9.8 Hz), 4.80 (1H, d, J=12.0 Hz), 4.67 (1H, d, J=12.0 Hz), 4.9-4.7 (1H, m), 4.2-4.1 (4H, m), 3.6-3.35 (2H, m), 1.32 (3H, t, J=7.0 Hz), 1.29 (3H, t, J=7.4 Hz); $^{13}$C NMR (CDCl$_3$) δ=195.1 (s), 154.0 (s), 135.0 (s), 132.1 (s), 129.7 (s), 128.9 (s), 95.3 (s), 74.8 (s), 63.3 (d, J=7.5 Hz), 62.9 (d, J=7.4 Hz), 44.5 (d, J=160.5 Hz), 38.3 (s), 16.5 (d, J=5.8 Hz), 16.3 (d, J=5.8 Hz); IR 3233, 3049, 2987, 1739, 1698, 1614, 1531, 1478, 1440, 1392, 1352, 1228, 1147, 1093, 1031, 970, 887, 819, 735, 545 cm$^{-1}$; HRMS (FAB); Exact mass calcd for C$_{16}$H$_{21}$Cl$_5$N$_2$O$_8$P [M+H]$^{+,}$ 505.0101. Found 505.0123; Chiral HPLC, Daicel Chiralcel AD, hexane/iPrOH=9/1, flow rate=1.0 mL/min; t$_R$=28.3 min (minor, R), t$_R$=53.0 min (major, S)

(1S)-[3-Oxo-1-(2,2,2-trichloro-ethoxycarbonylamino)-butyl]-phosphonic acid diethyl ester (4k): [α]$^{23}_D$–3.61 (89% ee, c 1.16, CHCl$_3$); $^1$H NMR (CDCl$_3$) δ=6.2-5.4 (1H, m), 4.8 (1H, d, J=11.9 Hz), 4.69 (1H, d, J=11.9 Hz), 4.6-4.4 (1H, m), 4.3-4.0 (4H, m), 2.94 (1H, d, J=7.0 Hz), 2.90 (1H, d, J=6.4 Hz), 2.22 (3H, s) 1.332 (3H, t, J=7.0 Hz), 1.326 (3H, t, J =7.0 Hz); $^{13}$C NMR (CDCl$_3$) δ=195.1 (s), 154.0 (s), 135.0 (s), 132.1 (s), 129.7 (s), 128.9 (s), 95.3 (s), 74.8 (s), 63.3 (d, J=7.5 Hz), 62.9 (d, J=7.4 Hz), 44.5 (d, J=160.5 Hz), 38.3 (s), 16.5 (d, J=7.4 Hz), 16.3 (d, J=5.8 Hz); IR 3437, 3053, 2988, 1735, 1643, 1542, 1400, 1369, 1226, 1149, 1095, 1032, 968, 819, 729, 544 cm$^{-1}$; HRMS (FAB); Exact mass calcd for C$_{11}$H$_{20}$Cl$_5$NO$_6$P [M+H]$^{+,}$ 398.0094. Found 398.0087

(3S)-3-(Diethoxy-phosphoryl)-3-(2,2,2-trichloro-ethoxycarbonylamino)-thiopropionic acid S-tert-butyl ester (4l): [α]$^{28}_D$–10.68 (90% ee, c 2.83, CHCl$_3$); $^1$H NMR (CDCl$_3$) δ=5.90-5.75 (1H, m), 4.77 (1H, d, J=12.0 Hz), 4.72 ($^1$H, d, J=12.2 Hz), 4.65-4.50 (1H, m), 4.25-4.05 (4H, m), 3.10-2.75 (2H, m), 1.45 (3H, s), 1.332 (3H, t, J=7.1 Hz), 1.329 (3H, t, J=7.1 Hz); $^{13}$C NMR (CDCl$_3$) δ=196.0 (d, J=18.9 Hz), 153.9 (d, J=7.4 Hz), 95.3 (s), 74.7 (s), 63.2 (d, J=9.0 Hz), 62.9 (d, J=8.2 Hz), 48.7 (s), 46.2 (s), 44.1 (s), 43.6 (s), 43.5 (s), 29.6 (s), 16.4, 16.4, 16.3 IR cm$^{-1}$; Chiral HPLC, Daicel Chiralcel AD, hexane/iPrOH=19/1, flow rate=0.5 mL/min; t$_R$=34.1 min (minor, R), t$_R$=38.3 min (major, S); Anal. Calcd for C$_{14}$H$_{25}$Cl$_3$NO$_6$PS C: 35.57 H: 5.33 N: 2.96, Found C: 35.30 H: 5.08 N: 3.02

EXAMPLE 2

Silyl Enol Ether Addition Reaction with an Iminophosphonic Acid Diester Using a Chiral Copper Catalyst Without the Co-presence of HFIP Methylene chloride (1.5 ml) was added to copper triflate (20 μmoles) and a chiral diamine (22 μmoles), and the reaction mixture was agitated for 6 hours at room temperature. Molecular sieve 3A (10 mg) was added, and the reaction mixture was subsequently cooled to 0° C. A methylene chloride (1 ml) solution of a silyl enol ether (2a, 0.1 mmole) was added. A methylene chloride (0.1 M, 2 ml) solution of the N-protected-α-iminophosphonic acid diester obtained in Production Example 1 and a methylene chloride (2 ml) solution of a silyl enol ether (0.2 mmole) again were slowly (ordinarily over eight hours) added dropwise. The reaction mixture was agitated for an additional hour. The reaction solution was poured into a saturated aqueous solution of sodium bicarbonate and was agitated vigorously until the organic layer changed to blue. The organic layer was extracted using methylene chloride. The organic layers were combined, washed using saturated aqueous sodium chloride solution and dried using anhydrous sodium sulfate. The solvent was removed by distillation under reduced pressure, the residue was dissolved in methylene chloride (2 ml) and HF-pyridine (several drops) was added. A saturated aqueous sodium of sodium bicarbonate was added, the solution was extracted several times using methylene chloride and the organic layers were combined, washed using saturated aqueous sodium chloride solution and dried over anhydrous sodium sulfate. The solvent was removed by distillation under reduced pressure, and the residue was purified using silica gel chromatography to obtain a desired N-protected-α-amino-γ-oxophosphonic acid diester derivative. The results are shown in Table 1 (Entry 1).

What is claimed is:

1. A production method for aminophosphonic acid derivatives comprising reacting an α-iminophosphonate ester represented by the formula

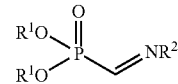

wherein R$^1$ represents an alkyl group and R$^2$ represents a protective group for an amino group, and a nucleophilic agent in the presence of a chiral copper catalyst represented by the formula

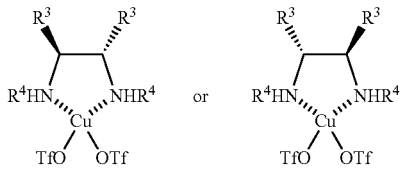

wherein R$^3$ and R$^4$, may be identical or different, represent an aryl group or an aralkyl group.

2. The production method of claim 1, wherein the nucleophilic agent is a silyl enol ether represented by the formula

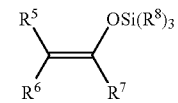

wherein R$^5$ and R$^6$, may be identical or different, represent hydrogen atoms, alkyl groups, aryl groups or aralkyl groups, R$^7$ represents an alkyl group, aryl group, aralkyl group, alkoxy group or sulfide group represented by —SR$^9$, wherein R$^9$ represents an alkyl group or an aryl group, and R$^8$, may be identical or different, represents an alkyl group or a phenyl group.

3. The production method of claim 1, wherein a compound having an activated proton is added to the reaction medium as an additive.

4. The production method of claim 3, wherein the additive is hexafluoro isopropyl alcohol (HFIP).

5. The production method of claim 1, wherein the aminophosphonic acid derivative is represented by the formula

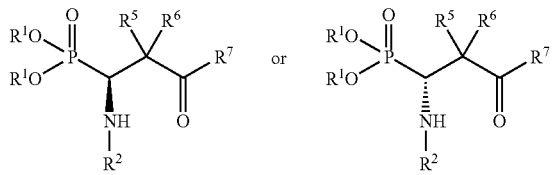

wherein, $R^1$ represents an alkyl group, $R^2$ represents a protective group for an amino group, $R^3$ and $R^4$, which may be identical or different, each represent an aryl group or an aralkyl group, $R^5$ and $R^6$, which may be identical or different, each represent hydrogen atoms, alkyl groups, aryl groups or aralkyl groups, and $R^7$ represents an alkyl group, aryl group, aralkyl group, alkoxy group or sulfide group represented by —$SR^9$, wherein $R^9$ represents an alkyl group or an aryl group.

6. The production method of claim 2, wherein a compound having an activated proton is added to the reaction medium as an additive.

7. The production method of claim 6, wherein the additive is hexafluoro isopropyl alcohol (HFIP).

8. The production method of claim 2, wherein the aminophosphonic acid derivative is represented by the formula

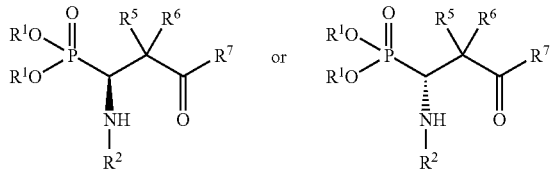

wherein, $R^1$ represents an alkyl group, $R^2$ represents a protective group for an amino group, $R^3$ and $R^4$, which may be identical or different, each represent an aryl group or an aralkyl group, $R^5$ and $R^6$, which may be identical or different, each represent hydrogen atoms, alkyl groups, aryl groups or aralkyl groups, and $R^7$ represents an alkyl group, aryl group, aralkyl group, alkoxy group or sulfide group represented by —$SR^9$, wherein $R^9$ represents an alkyl group or an aryl group.

9. The production method of claim 3, wherein the aminophosphonic acid derivative represented by the formula

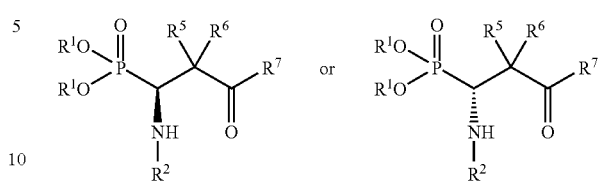

wherein, $R^1$ represents an alkyl group, $R^2$ represents a protective group for an amino group, $R^3$ and $R^4$, which may be identical or different, each represent an aryl group or an aralkyl group, $R^5$ and $R^6$, which may be identical or different, each represent hydrogen atoms, alkyl groups, aryl groups or aralkyl groups, and $R^7$ represents an alkyl group, aryl group, aralkyl group, alkoxy group or sulfide group represented by —$SR^9$, wherein $R^9$ represents an alkyl group or an aryl group.

10. The production method of claim 4, wherein the aminophosphonic acid derivative represented by the formula

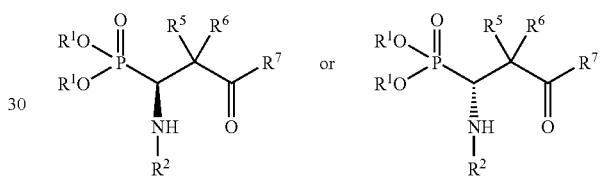

wherein, $R^1$ represents an alkyl group, $R^2$ represents a protective group for an amino group, $R^3$ and $R^4$, which may be identical or different, each represent an aryl group or an aralkyl group, $R^5$ and $R^6$, which may be identical or different, each represent hydrogen atoms, alkyl groups, aryl groups or aralkyl groups, and $R^7$ represents an alkyl group, aryl group, aralkyl group, alkoxy group or sulfide group represented by —$SR^9$, wherein $R^9$ represents an alkyl group or an aryl group.

* * * * *